United States Patent [19]

Takasu

[11] 4,291,990

[45] Sep. 29, 1981

[54] APPARATUS FOR MEASURING THE DISTRIBUTION OF IRREGULARITIES ON A MIRROR SURFACE

[75] Inventor: Shinichiro Takasu, Tokyo, Japan

[73] Assignee: VLSI Technology Research Association, Japan

[21] Appl. No.: 5,199

[22] Filed: Jan. 22, 1979

[30] Foreign Application Priority Data

Jan. 27, 1978 [JP] Japan ................................. 53-8086

[51] Int. Cl.³ ..................... G01N 21/55; G01B 11/30; G01B 9/02; G01N 21/00
[52] U.S. Cl. .................................. 356/445; 356/371; 356/354; 356/237
[58] Field of Search .............. 356/445, 446, 448, 371, 356/376, 124, 354, 355, 356, 237

[56] References Cited

U.S. PATENT DOCUMENTS 3,439,988 4/1969 Breske ............................ 356/371 X

OTHER PUBLICATIONS

Takasu et al., "Invited: Induced Defects in Crystals Through Mechanical Processing," Proceedings of the 6th Conference on Solid State Devices, Tokyo, 1974, pp. 261-263.

Primary Examiner—Vincent P. McGraw
Assistant Examiner—Rodney B. Bovernick
Attorney, Agent, or Firm—Finnegan, Henderson, Farabow, Garrett & Dunner

[57] ABSTRACT

An optical apparatus for measuring irregularities on the mirror surface of, for example, a silicon wafer used to provide a semiconductor integrated circuit. Irradiates on the mirror surface light fluxes arranged in a special form, for example, in the lattice form. By observing the pattern of light fluxes reflected from said mirror surface, one can measure the surface irregularities. A light flux issued from a light source is divided by a photomask or diffraction grating into first light fluxes irradiated all over the mirror surface and second light fluxes surrounding the respective first light fluxes in the continuous or discontinuous annular form, thereby ensuring the simultaneous measurement of the distribution of extensive irregularities over the entire mirror surface by the first light fluxes and the distribution of local irregularities on said mirror surface by the second light fluxes.

14 Claims, 18 Drawing Figures

F I G. 10
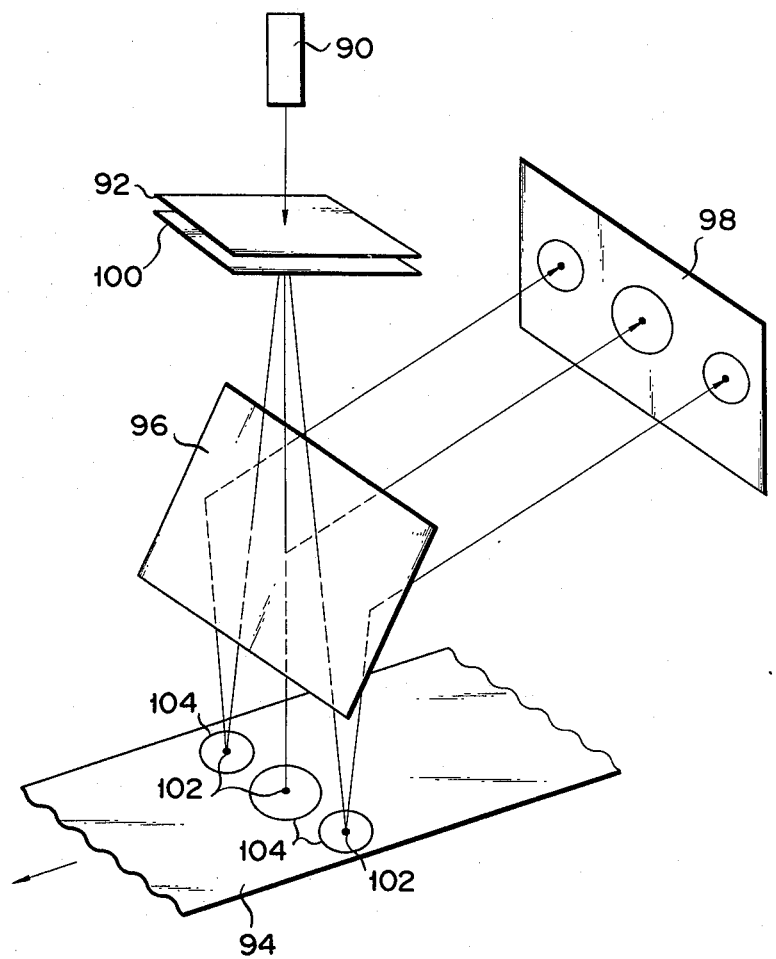

APPARATUS FOR MEASURING THE DISTRIBUTION OF IRREGULARITIES ON A MIRROR SURFACE

BACKGROUND OF THE INVENTION

This invention relates to an apparatus for measuring irregularities on a plane, and more particularly to an apparatus for measuring the distribution of irregularities on a mirror surface by optically examining irregularities occurring in part of said surface or strains appearing in the whole thereof.

Where a semiconductor integrated circuit is manufactured, the flatness of the surface of a silicon wafer generally has a close relationship with the reliability of the circuit. The measurement of irregularities on a mirror surface of, for example, a wafer has been carried out by an optical method like that based on interference fringes. This method is to observe interference fringes produced by different paths of light beams reflected from a mirror surface and also from a glass plate placed thereon. If the mirror surface is strained, then reflections from the respective parts of the mirror surface will vary in direction and in the length of light path, resulting in irregular interference fringes. Therefore, the distribution of irregularities on the mirror surface can be measured by observing the irregular interference fringes. The above-mentioned method can indeed measure extensive strains over the whole of a mirror surface, but fails to find local irregularities. Detection of local irregularities has to be carried out by a time-consuming process of analyzing an interference pattern made into a readily observable form.

Other known optical methods include the multidivision method (Supplement to the Journal of the Japan Society of Applied Physics, vol. 44, 1975, P. 261) which comprises the steps of dividing a laser beam by a plane lattice and determining the distribution of irregulaties on a mirror surface from a pattern of divided laser beams reflected from the mirror surface. Another known method is the MOIRE' infringement method which comprises the steps of superimposing two plane lattices having the same lattice constant with their relative positions displaced through a slight angle and observing the resultant MOIRE' infringements. However, all the prior art methods fail to visually measure local irregularities on a mirror surface, though they are capable of examining extensive strains over the whole of said mirror surface.

Further, there has been developed a method like a photomicrometer which chiefly examines local irregularities on a mirror surface conversely from the above-mentioned prior art methods. In that method the photomicrometer is used to attempt to examine strains occurring all over a mirror surface. Then observation spots spread over the entire mirror surface have to be scanned, thus consuming a considerable length of time.

During manufacture of an integrated circuit, an impurity is diffused in a silicon wafer in a diffusion furnace. Therefore, it is preferred that measurement of irregularities on the mirror surface of the silicon wafer be carried out while the wafer is placed in the diffusion furnace. A mechanical method like a contact method presents difficulties in attaining the above-mentioned object.

SUMMARY OF THE INVENTION

It is accordingly an object of this invention to provide an apparatus for measuring the distribution of irregularities on a mirror surface which can optically or visually measure not only local but also extensive strains on the mirror surface. Another object of the invention is to provide an apparatus for measuring the distribution of irregularities on the mirror surface of a wafer in real time by a remote measuring process while an integrated circuit is manufactured.

According to the invention, there is provided a mirror surface irregularities-measuring apparatus which comprises a light source for irradiating light fluxes on a mirror surface; means for dividing a light flux sent forth from the light source into first light fluxes irradiated extensively all over the mirror surface and second light fluxes which are locally irradiated on the mirror surface to concentrically surround the respective first light fluxes; and light-receiving means for detecting light fluxes reflected from the mirror surface. While a light source may be of any type, it is necessary to use such a light source as produces interference fringes, particularly where a diffraction phenomenon is utilized as the dividing means. A process of using a photomask and projecting a mask pattern itself on an object of measurement may be applied as light flux-dividing means. The first light flux may be a single ray, but should preferably be formed of a plurality of light fluxes arranged in the lattice form. The second light fluxes are preferred to concentrically surround the respective first light fluxes. The light-receiving means well serves the purpose, if it allows for the visual projection of light fluxes on the ordinary screen. It is possible to electrically measure irregularities on a mirror surface by providing the screen with photoelectric elements.

BRIEF DESCRIPTION OF THE DRAWING

FIG. 10 illustrates the operation of a still further embodiment of the invention using a one-dimensional diffraction lattice.

DETAILED DESCRIPTION OF THE PREFERRED EMBODIMENTS

Figure 1:
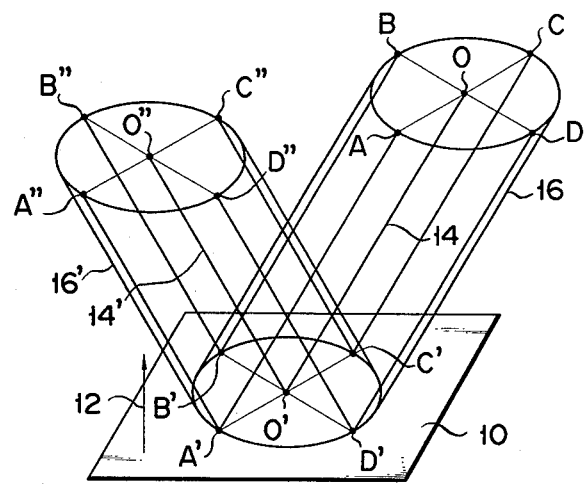
FIG. 1 shows the principle on which this invention is based, when a mirror surface is completely flat.
Figure 2:
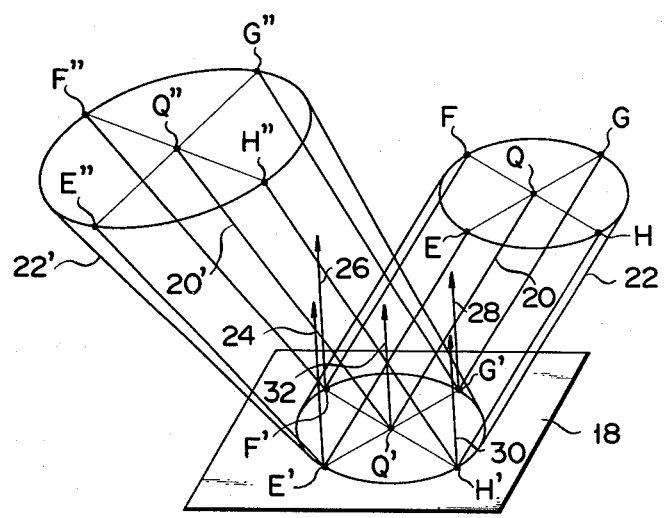
FIG. 2 indicates the principle of this invention by which measurement is made of the distribution of irregularities on a mirror surface.

This invention utilizes the law of light reflection. FIGS. 1 and 2 show the principle on which the invention is based. FIG. 1 represents the case where a mirror surface 10 is completely flat. The normals 12 of the mirror surface 10 indicate the same direction throughout said mirror surface 10. Where two light fluxes 14, 16 arrive on the mirror surface 10. Then two reflected light fluxes 14', 16' are produced. The light flux 14 is a first light flux constituting a core. The second light fluxes 16 are arranged in the hollow cylindrical form concentrically surrounding the first light flux 14. The reflected light fluxes 14', 16' have the same relationship. For convenience of description, the incoming and reflected light fluxes are indicated in section. Point O' on the mirror surface 10 and point O'' on the reflected light flux 14' are defined to correspond to point O on the first incoming light flux 14. Similarly, points A', B', C', D' on the mirror surface 10 and points A'', B'', C'', D'' of the reflected light fluxes 16' are defined to correspond to points A, B, C, D of the second light fluxes 16. Now let it be assumed that the plane ABCD of the incoming light flux and the plane A''B''C''D'' of the reflected light flux are parallel with the mirror surface 10. Then, the figures ABCD, A'B'C'D', A''B''C''D'' are congruent with each other. Unless the planes ABCD and A''B''C''D'' are parallel with the mirror surface 10, the congruent relationship between these planes is lost. Where, however, the planes ABCD, A''B''C''D'' are chosen to be perpendicular to the light fluxes OO', O''O'', then the figures ABCD, A''B''C''D'' are congruent with the figure A'B'C'D'.

FIG. 2 shows the principle of this invention by which measurement is made of the distribution of irregularities on a mirror surface 18, with the above-mentioned relationship taken into account. As in FIG. 1, when two light fluxes 20, 22 arrive, then two reflected light fluxes 20', 22'' are produced. The light flux 20 is a first light flux constituting a core. The light flux 22 is formed of second light fluxes arranged in the hollow cylindrical form concentrically surrounding the first light flux 20. As in FIG. 1, points are defined which indicate the relationship between the incoming and reflected light fluxes. Reference numerals 24, 26, 28, 30, 32 denote normals at points E', F', G', H', Q' on the mirror surface 18. Now let it be assumed that irregularities appear near a figure E'F'G'H'. Then the normals 24, 26, 28, 30, 32 are not parallel with each other. In such case, the figures EFGH and E''F''G''H'' are not congruent with each other, even if the plane EFGH of an incoming light flux and the plane E''F''G''H'' of a reflexed light flux are parallel with the mirror surface 18. Further, even if the planes EFGH and E''F''G''H'' are chosen to be perpendicular to light fluxes QQ', Q'Q'' the figures EFGH and E''F''G''H'' are not congruent with each other. The change of the figure EFGH to the figure E''F''G''H'' is defined by the normals at points E', F', G', H'.

Where the first core light flux and the second light fluxes arranged in the prescribed form surrounding the first light flux are irradiated on the mirror surface whose condition is to be measured, and comparison is made between a pattern of incoming light fluxes and a pattern of reflected light fluxes thereof, then it is possible to measure the distribution of irregularities on the mirror surface, as can be understood from the foregoing description. If the first light flux is formed of a plurality of beams instead of a single beam and the second light fluxes are so arranged as to concentrically surround the first flux, then it is possible to determine the distribution of extensive irregularities on the mirror surface from a pattern of reflections from the first light flux, and also define the distribution of local irregularities on the mirror surface from a pattern of reflections from the second light fluxes.

The second hollow cylindrical light fluxes may be replaced by hollow round conical light fluxes formed by setting points A, B, C, D of FIG. 1 convergently at point O and similarly setting points E, F, G, H of FIG. 2 convergently at point Q. This arrangement differs from the preceding case only in that the outlines of figures associated with incoming and reflected light fluxes are changed from congruent to similar. Further, the second light fluxes need not be arranged in the fully continuous annular sectional form, but may have a discontinuous annular sectional form. The second light fluxes need not be arranged in the continuous circular sectional form but may have such a sectional form as is defined by the optical points of, for example, a polygon.

The vital point of this invention is that a light flux sent forth from a light source is divided into a first flux and a plurality of second fluxes concentrically surrounding the first light flux. Various light flux-dividing processes have been devised for the invention. There will now be described by reference to the appended drawing the preferred embodiments of the apparatus of this invention for measuring the distribution of irregularities on a mirror surface.

Figure 3B:
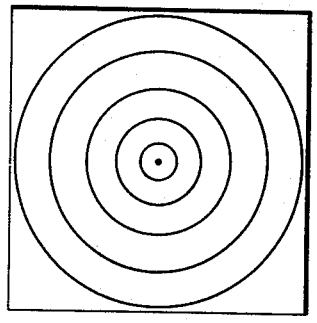
FIGS. 3B and 3C show two forms of a photomask.
Figure 3C:
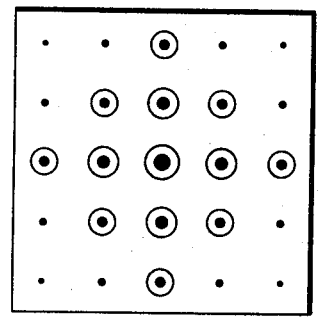
Figure 3A:
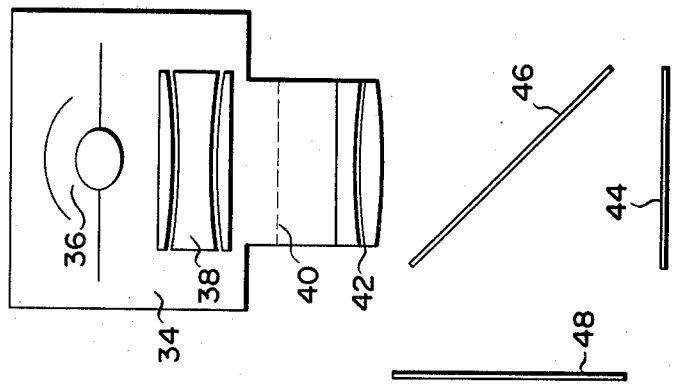
FIG. 3A illustrates the schematic arrangement of one embodiment of the invention using a photomask.

Description is first given of a light-projecting process in which a light flux is divided by means of a photomask and lens into the prescribed form in which a first divided light flux is concentrically surrounded by a plurality of second divided fluxes. FIG. 3A shows the schematic arrangement of the above-mentioned light flux-dividing apparatus. A light source 36 is received in a lamp house 34. A light flux issued from the light source 36 is converged by a condenser lens 38. The converged light fluxes are divided into first and second light fluxes by a photomask 40 having a prescribed perforated pattern. The divided light fluxes are irradiated through a projection lens 42, for example, on the polished surface of a semiconductor wafer 44. Light fluxes reflected from the surface of the semiconductor wafer 44 are projected on a screen 48 by means of a half mirror 46, thereby visually measuring the distribution of irregularities on the mirror surface of the polished semiconductor wafer 44. If the photomask 40 is of such type as is shown in FIGS. 3B or 3C, (the portions smeared in black are permeable to light), then it is possible to visually determine the distribution of extensive and local irregularities on a mirror surface at the same time from the deformation of the second light fluxes arranged in the annular form.

Figure 4:
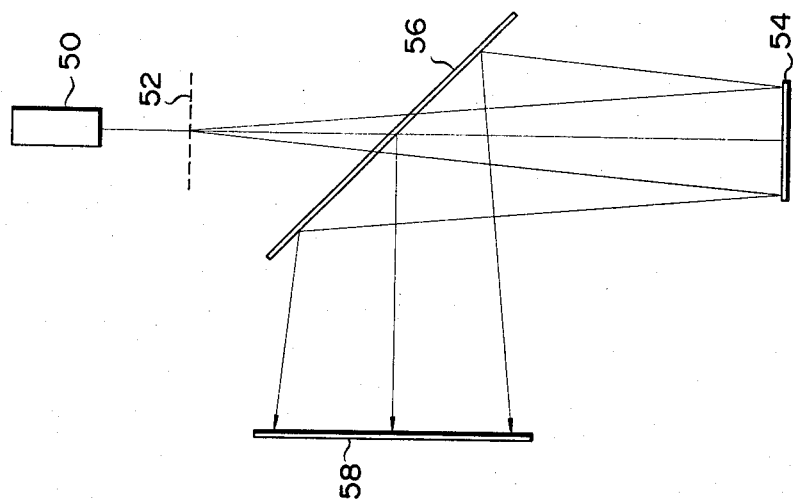
FIG. 4 indicates the schematic arrangment of another embodiment of the invention using a diffraction grating.

There will now be described the process of dividing a light flux by means of a diffraction grating. FIG. 4 indicates the schematic arrangement of that process. A coherent light flux such as a laser beam irradiated from a source 50 is divided into first and second light fluxes by means of a diffraction grating 52. The first and second divided light fluxes are projected on the mirror surface of a material 54 whose surface condition is to be measured. Light fluxes reflected from the mirror surface are projected on a screen 58 by means of a half mirror 56, thereby measuring the distribution of irregularities, if any, on the mirror surface.

Figure 5A:
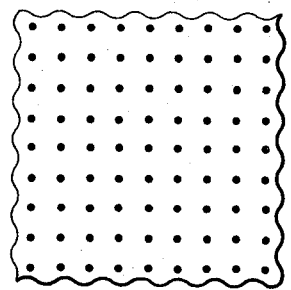
FIG. 5A is a square lattice.

It is known that where a plane lattice is irradiated by a coherent light flux, diffracted light beams are produced. Where a square plane shown (in FIG. 5A is used in which black spots are impermeable to light), then a diffraction pattern derived therefrom is formed of light fluxes arranged in the lattice form shown in FIG. 5B. A pattern (FIG. 5B) of irradiated light fluxes (in which black spots denote the respective irradiated light fluxes) makes it possible to measure the distribution of extensive irregularities on a mirror surface, but fails to supply data on irregularities occurring in the minute local portions of the mirror surface.

Figure 6A:
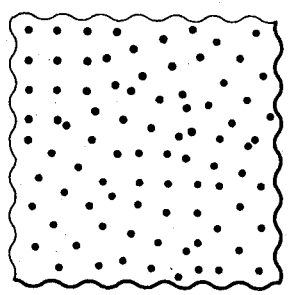
FIG. 6A is a plane multiregion lattice.
Figure 6B:
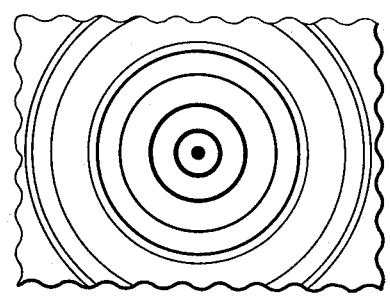
FIG. 6B is a diffraction pattern derived from said multiregion lattice.

For measurement of local irregularities, therefore, this invention applies a plane multiregion lattice constructed by dividing a plane lattice into a plurality of minute regions assembled in an irregular form. As used herein, the term "plane multiregion lattice" is defined to mean that type in which the respective minute regions have a regular lattice arrangement, but are distributed in irregular directions. Now let it be assumed that a coherent light flux is irradiated on such plane multiregion lattice. If, in this case, the respective minute regions have a sufficiently smaller size than the diameter of an incoming light flux, then a diffracted light flux forms diffraction rings (FIG. 6B). FIG. 6A is an enlarged view of the plane multiregion lattice. FIG. 6B indicates a diffraction pattern thereof. Where the concentrically arranged diffraction rings are irradiated on a mirror surface, in which irregularities are supposedly formed, then changes occur in the direction in which the diffraction rings of light fluxes are reflected from the mirror surface. Therefore, irregularities on the mirror surface can be determined from these changes.

Further, where a plurality of first core light fluxes are arranged in the lattice form and a plurality of second light fluxes are made to concentrically surround the first light fluxes, then extensive strains on a mirror surface can be detected from the displacement of the first light fluxes from linearity, and local irregularities on the mirror surface can be measured from the displacement from roundness of the second light fluxes arranged in the annular form. For generation of the above-mentioned two types of light flux, it is advised to superimpose two lattices and utilize double diffraction derived therefrom.

Figure 5B:
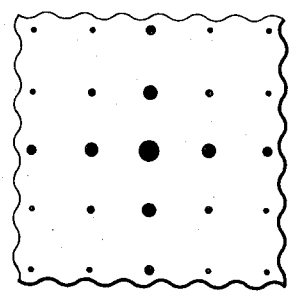
FIG. 5B is a diffraction pattern obtained from a square lattice.
Figure 7A:
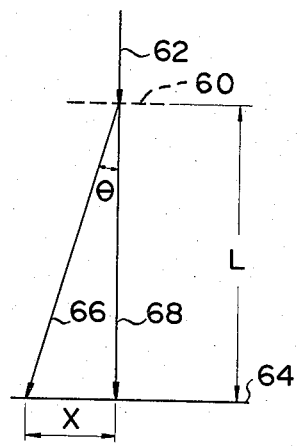
FIGS. 7A and 7B illustrate the operation of still another embodiment of the invention utilizing double diffraction.

There will now be described a typical embodiment using an assembly of the aforesaid square lattice and plane multiregion lattice. Description is given by reference to FIG. 7A of the concrete design conditions under which the first light fluxes alone are produced by diffraction through the square lattice. Reference numeral 60 is a square lattice. A coherent light flux 62 such as a laser ray is irradiated on the square lattice 60. Then the diffracted light flux is irradiated on the mirror surface of a sample 64 in the form of a square lattice as illustrated in FIG. 5B. In this case, a first diffracted light flux 66 enters the sample 64 at an angle $\theta$ to another diffracted light flux 68 of the zero order. With $\lambda$ taken to denote the wavelength of an incoming coherent light flux 62; and d taken to represent the lattice constant of the square lattice 60, then there results $$\sin \theta = \lambda/d$$

With X taken to show a distance between the two points at which the diffracted light flux 68 of the zero order and the first diffracted light flux 66 enter the mirror surface of the sample 64; L to show a distance between the plane lattice 60 and sample 64; and assuming X<0.1L, then there results $$X/L \approx \sin \theta = \lambda/d$$

Where, therefore, the coherent light flux 62 consists of a He-Ne laser beam, and assuming $\lambda=0.63$ microns and X/L=0.05, then the lattice constant d is expressed as $d \approx 12.6$ microns. Now let it be assumed that measurement is made of the condition of the mirror surface of the sample 64 consisting of a silicon wafer having a diameter of about 100 mm. Where, in this case, the mirror surface of said sample 64 is irradiated by a single diffracted light flux of the zero order, four first diffracted light fluxes and four second diffracted light fluxes, then it is advised to chose a distance between the square lattice 60 and sample 64 to be 40 to 48 cm in order to satisfy the aforesaid formula $X/L \approx \sin \theta = \lambda/d$, because the above-mentioned character X indicates 20 to 24 mm.

Figure 7B:
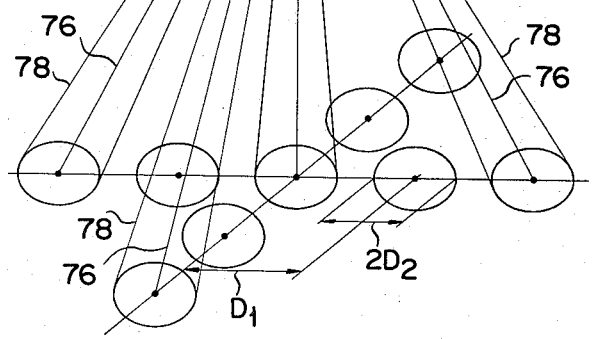

As seen from the illustration of FIG. 7B, a first lattice 70 (a square lattice) and a second lattice 72 (a plane multiregion lattice) are spacially superimposed to carry out double diffraction. As a result, the respective first light fluxes 76 diffracted from the first square lattice 70 which are arranged in the lattice form are each surrounded by a hollow conical second light flux 78, providing a required diffraction pattern.

Figure 7C:
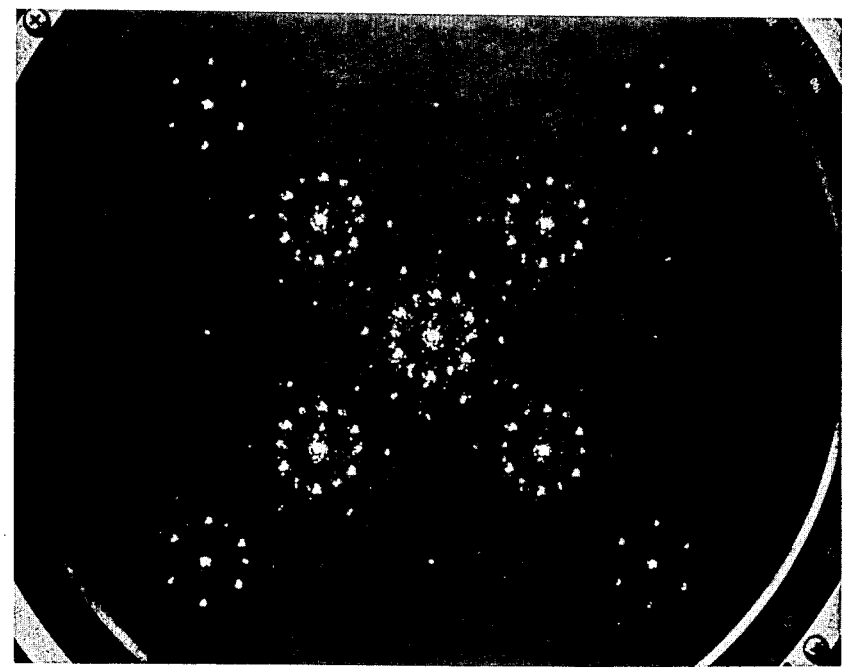
FIGS. 7C and 7D is a diffraction pattern obtained from the embodiment described in FIGS. 7A and 7B.
Figure 7D:
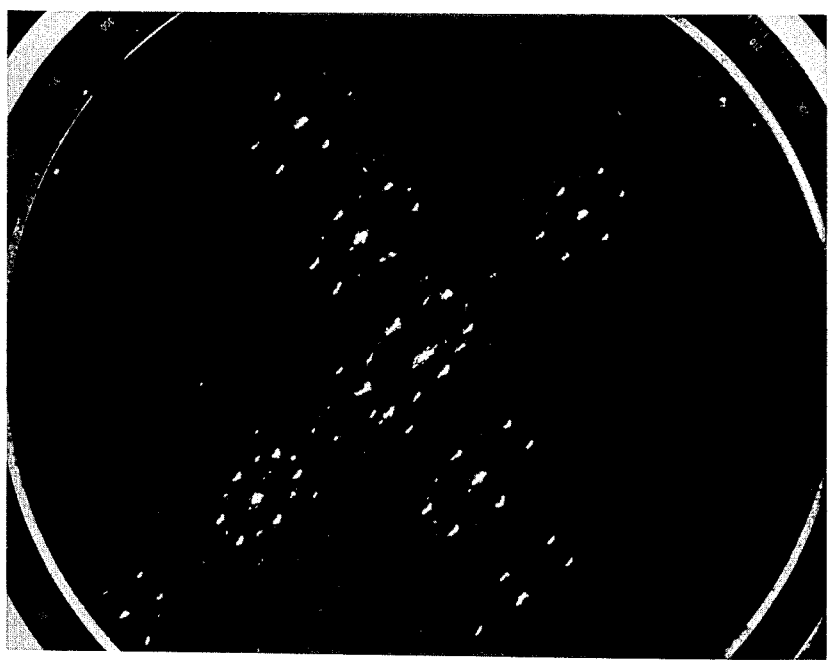

For generation of the second light fluxes 78 surrounding the first light flux 76, it is possible to use a different type of lattice from the plane multiregion lattice. Namely, it is possible to use a square lattice as a first lattice and a hexagonal lattice having a larger lattice constant than the first lattice as a second lattice. Where a coherent light flux is introduced with both lattices so disposed as to carry out double diffraction, then second fluxes so arranged as to collectively indicate a discontinuous annular form are projected concentrically around the respective first fluxes, as illustrated in FIG. 7C. If there are some distribution on a mirror surface, the reflected diffraction pattern is seen in FIG. 7D.

Referring to the projection pattern of FIG. 7B, if a given second light flux surrounding the corresponding first light flux happens to be superimposed on another second light flux, then it is impossible to exactly measure the distribution of desired local irregularities on a mirror face. With $D_1$ taken to indicate a distance between the respective adjacent first light fluxes, and $2D_2$ taken to represent the diameter of an annular form defined by the respective second light fluxes as shown in FIG. 7B, then it is preferred to ensure the relationship of $D_1 > 2D_2$. With $d_1$ taken to indicate the lattice constant of the first lattice from which the first light flux is diffracted, and $d_2$ taken to denote the lattice constant of the second lattice from which the second light flux is diffracted, the relationship of $d_1 < 2d_2$ serves to satisfy the aforesaid relationship of $D_1 > 2D_2$. The reason is that the lattice constant of the first lattice is inversely proportional to the distance $D_1$ of the respective adjacent first light fluxes diffracted from said first lattice.

If, in case double diffraction is carried out by a combination of a plane lattice and a plane multiregion lattice, the lattice constant $d_2$ of the second plane multiregion lattice is enlarged to reduce the diameter $D_2$ of the annular form defined by the respective second light fluxes, then a number of lattice points included in the respective minute regions of the plane multiregion lattice decreases, leading to the enlargement of the width of a diffraction ring. With the width of a diffraction ring expressed by a half band width δ, then there approximately results $$\delta \propto \lambda/\overline{N}$$

where:
λ=a wavelength of an incoming light flux
$\overline{N}$=an average number of lattice points included in the respective minute regions of the plane multiregion lattice Where the diameter $D_2$ of the annular form defined by the second diffracted light fluxes is reduced to one-fifth of the distance $D_1$ between the respective first adjacent diffracted light fluxes, then there results $$d_2 = 5d_1 = 63 \text{ microns}$$

where the lattice constant $d_1$ of the first square lattice indicates 12.6 microns as previously described. With $\delta_1$ taken to denote the width of the diffraction ring, and $\delta_2$ taken to represent the width of the diffraction ring when all the lattice points take part in diffraction, the ratio of $\delta_1$ to $\delta_2$ is expressed as follows:

$$\delta_1/\delta_2 = \frac{\lambda/\overline{N}}{\lambda/25 \times \overline{N}} = 25$$

Where the lattice constant is thus enlarged, then the width of a diffraction ring is broadened in proportion to the square of said lattice constant. The broadening of the width of the diffraction ring at the reduction of the diameter thereof results in a decline in a capacity of resolving a diffracted light flux and consequently gives rise to errors in measuring the distribution of local irregularities on a mirror surface.

Figure 8:
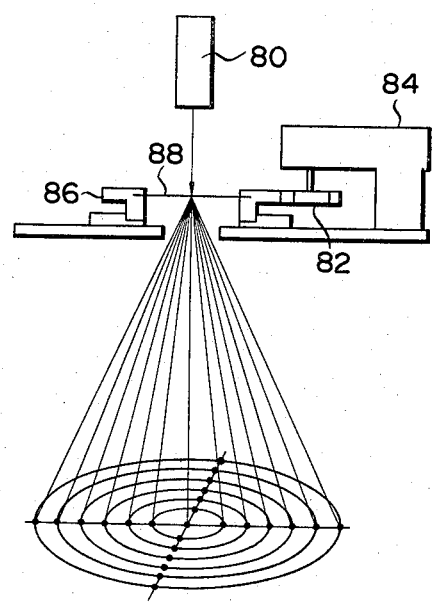
FIG. 8 illustrates the operation of a further embodiment of the invention which carries out double diffraction while a plane lattice is rotated about an output axis.
Figure 8:
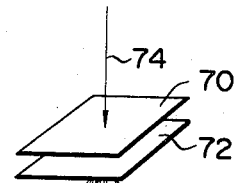

There are some means of resolving the above-mentioned difficulties to carry out double diffraction with the width of a diffraction ring decreased. For instance, it is possible equivalently to increase a number of lattice points by rotating a single diffraction grating as shown in FIG. 8. FIG. 8 illustrates the embodiment in which a single plane lattice is rotated to produce an annular diffracted light flux. A coherent light flux issued from a source 80 enters a plane lattice 88 mounted on a turn table 86 rotated by means of a gear 82 fitted to the peripheral surface of a drive motor 84. Now let it be assumed that an incoming light consists of a He-Ne laser beam; the plane lattice 88 is formed of a square lattice having a lattice constant of 21 microns; and a distance between the plane lattice 88 and the mirror surface of a sample is 500 mm. Where in this case the plane lattice 88 is not rotated, then projected light spots are produced on the mirror surface of the sample in the form of a square lattice having lattice points arranged at a interval of 15 mm. Where the plane lattice 88 is rotated, then the respective projected light spots define annular loci (FIG. 8), as in the case of the aforesaid plane multiregion lattice. In this case, the first innermost diffraction ring appearing on the mirror surface of the sample has a radius of 15.0 mm; the second diffraction ring a radius of 21.2 mm; the third diffraction ring a radius of 30.0 mm; the fourth diffraction ring a radius of 33.5 mm . . . ; and the ninth diffraction ring a radius of 60.0 mm. The embodiment of FIG. 8 presents difficulties in detecting local irregularities on a mirror surface, through capable of measuring extensive irregularities thereon. It is therefore preferred to superimpose a first square lattice for producing first light fluxes arranged in the lattice form, for example, on a second rotatable square lattice having a larger lattice constant than the first lattice and cause second hollow conical light fluxes to surround the respective first lattice-arranged light fluxes. If the first stationary square lattice is made to have a lattice constant of 21 microns and the second rotatable square lattice is made to have a lattice constant of 63 microns, then a desired light flux pattern can be produced as in the foregoing embodiment illustrated in FIG. 7C.

Figure 9A:
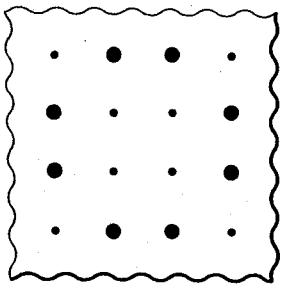
FIG. 9A is a super lattice.
Figure 9B:
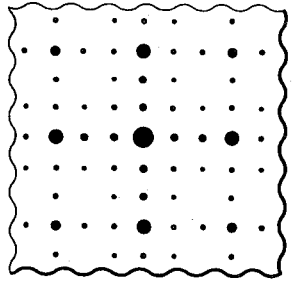
FIG. 9B is a diffraction pattern obtained from the super lattice.

There will now be described by reference to FIGS. 9A and 9B a further embodiment of this invention which eliminates the necessity of using a first stationary lattice and a second rotatable lattice to cause second hollow conical light fluxes to surround the respective first fluxes arranged in the lattice form by means of double diffraction. Where a super lattice of FIG. 9A is used which comprises a plurality of plane lattice of different lattice constants arranged on the same plane, then a diffraction pattern of FIG. 9B is produced. The plane lattices mounted on the same plane need not have the same shape. In other words, one group may be formed of square plane lattices and the other group thereof may consist of hexagonal plane lattices. In this case, first light fluxes are generated through the lattices having a smaller lattice constant. Second light fluxes are sent forth through the lattices having a larger lattice constant. Where a super lattice is formed, it is practically advantageous to cause lattices having a larger lattice constant to occupy a broader overall area, thereby increasing diffraction intensity. For the formation of the super lattice, it is necessary to consider the conditions for giving a full play to the missing orders. A single plane lattice which regularly changes in the lattice constant also acts like a super lattice.

A diffraction pattern can be determined from the lattice constant of its original lattice by the formula of Fourier transformation. Therefore, a pattern of reflected light fluxes which are actually irradiated on a mirror surface of an object under examination can be electrically compared with a theoretically calculated reflection pattern previously recorded on a screen to determine the presence or absence of irregularities on said mirror surface.

The foregoing description chiefly refers to the case where a square lattice was used. However, application of a hexagonal lattice can also attain the object of this invention. It is further possible to use a rhombordal or monoclinic lattice, according to the shape of a sample or the mode of measurement. For example, where measurement is made of the condition of the mirror surface of a continuously running bandshaped sample, it is advised to use a one-dimensional diffraction grating.

There will now be described this last-mentioned embodiment by reference to FIG. 10. A coherent light flux enters a one-dimensional diffraction lattice 92 from a source 90. The one-dimensional diffraction lattice 92 is so disposed as to cause a light flux diffracted therefrom to be irradiated on the mirror surface of a sample 94 at right angles to the direction to which the sample 94 is made to travel. A light flux reflected from the mirror surface is projected for visual observation on a screen 98 by means of a half mirror 96 inclined to the mirror surface of the sample 94 at an angle of 45°. Where, in this case, the aforesaid plane multiregion lattice 100 is set close to the one-dimensional lattice 92 to effect double diffraction, causing annular light fluxes to surround the one-dimensionally diffracted light flux, then it is possible to produce, as shown in FIG. 10, rings 104 of irradiated light fluxes surrounding the points 102 at which the one-dimensionally diffracted light flux is projected.

In all the foregoing embodiments, the second diffracted light fluxes are irradiated on a sample in the hollow conical form. However, it is possible to irradiate the second diffrected light fluxes on the sample in the hollow cylindrical form by applying a lens system.

What is claimed is:

1. An apparatus for measuring the distribution of extensive and local irregularities on a mirror surface comprising:
    light generating means for irradiating a coherent light flux onto said mirror surface;
    light dividing means, positioned between said light generating means and said mirror surface, for dividing the light flux irradiated from said light generating means into a plurality of first light fluxes, arranged in a prescribed lattice form to cover said mirror surface, for measuring extensive irregularities on said mirror surface and a plurality of second light fluxes, surrounding each of the first light fluxes but not overlapping or coinciding with each other, for measuring the distribution of local irregularities on the surface; and
    means for receiving light fluxes reflected from the mirror surface and for permitting the inspection of the pattern of reflections, whereby the distribution of extensive irregularities on the mirror surface are determined through the inspection of the pattern of reflections of the first light fluxes and the distribution of local irregularities on the mirror surface are determined through the inspection of the pattern of reflections from the second light fluxes.

2. The apparatus of claim 1 wherein said light dividing means includes a photomask provided with a plurality of holes arranged in a prescribed form for generating said first and second light fluxes.

3. The apparatus of claim 1 wherein said light dividing means comprises a diffraction grating.

4. The apparatus of claim 1 wherein said light dividing means includes two plane lattices disposed to execute double diffraction.

5. The apparatus of claim 4 wherein one of the plane lattices has a lattice constant which is at least twice as large as the lattice constant of the other lattice.

6. The apparatus of claim 4 wherein one plane lattice is a square lattice for generating the first light flux, and the other plane lattice is a plane multiregion lattice for generating the second light flux.

7. The apparatus of claim 6 wherein the multiregion lattice has a lattice constant which is at least twice as large as the lattice constant of said square lattice.

8. The apparatus of claim 4 wherein one lattice is a square lattice for generating the first light flux and the other lattice is a hexagonal lattice, having a larger lattice constant than the square lattice, for generating the second light flux.

9. The apparatus of claim 4 where one of said lattices is a first stationary square lattice for generating the first light flux and the other lattice is a second square lattice rotatably mounted for producing said second light flux upon its rotation.

10. The apparatus of claim 1 wherein said light flux dividing means comprises a super lattice comprised of a plurality of plane lattices of different lattice constants arranged on the same plane.

11. An apparatus for measuring the distribution of extensive and local irregularities on a mirror surface comprising:
    light generating means for irradiating a coherent light flux onto said mirror surface,
    a square lattice, positioned between said light generating means and said mirror surface, for dividing the light flux irradiated from said light generating means into a plurality of first light fluxes, arranged in a prescribed lattice form to cover said mirror surface, for measuring the extensive irregularities on said mirror surface
    a plane multiregion lattice positioned between said light generating means and said mirror surface and having a lattice constant that is at least twice as large as the lattice constant of said square lattice, for dividing the light flux irradiated from said light generating means into a plurality of second light fluxes, surrounding each of the first light fluxes but not overlapping or coinciding with each other, for measuring the distribution of local irregularities on the surface; and
    means for receiving light fluxes reflected from the mirror surface and for permitting the inspection of the pattern of reflections, whereby the distribution of extensive irregularities on the mirror surface are determined through the inspection of the pattern of reflections of the first light fluxes and the distribution of local irregularities on the mirror surface are determined through the inspection of the pattern of reflections from the second light fluxes.

12. The apparatus of claim 11 wherein the light generating means generates a laser beam.

13. The apparatus of claim 12 wherein said means for receiving and permitting inspection of said light fluxes includes a screen for viewing the reflected fluxes and a half mirror for directing the reflected fluxes from said mirror surface to said screen.

14. The apparatus of claim 12 further comprising means for electrically comparing the reflected fluxes with a standard to determine the distribution or irregularities on the mirror surface.

* * * * *

UNITED STATES PATENT AND TRADEMARK OFFICE
CERTIFICATE OF CORRECTION

PATENT NO.  : 4,291,990
DATED       : September 29, 1981
INVENTOR(S) : Takasu, Shinichiro It is certified that error appears in the above—identified patent and that said Letters Patent is hereby corrected as shown below:

IN THE ABSTRACT:

Change "Irradiates" to --The apparatus irradiates--.

Signed and Sealed this

Twenty-ninth Day of December 1981

[SEAL]

Attest:

GERALD J. MOSSINGHOFF

Attesting Officer        Commissioner of Patents and Trademarks